United States Patent [19]

Blythin

[11] Patent Number: 4,775,524
[45] Date of Patent: Oct. 4, 1988

[54] METHOD OF TREATING HYPERPROLIFERATIVE SKIN DISEASE WITH SUBSTITUTED HETEROSPIRO PYRIDINE DERIVATIVES

[75] Inventor: David J. Blythin, North Caldwell, N.J.

[73] Assignee: Schering Corporation, Kenilworth, N.J.

[21] Appl. No.: 938,196

[22] Filed: Dec. 5, 1986

[51] Int. Cl.$^4$ .............................................. A61K 31/44
[52] U.S. Cl. ..................................... 424/45; 514/248; 514/249; 514/278; 514/863

[58] Field of Search ............... 514/278, 248, 249, 863; 424/45

[56] References Cited

U.S. PATENT DOCUMENTS 4,632,923 12/1986 Blythin ................................ 514/247
4,652,564 3/1987 Blythin ................................ 514/248

Primary Examiner—Leonard Schenkman
Attorney, Agent, or Firm—Richard C. Billups; James R. Nelson; Stephen I. Miller

[57] ABSTRACT

A method of treating a mammal for hyperproliferative skin disease is disclosed, using substituted heterospiro pyridine derivatives.

23 Claims, No Drawings

METHOD OF TREATING HYPERPROLIFERATIVE SKIN DISEASE WITH SUBSTITUTED HETEROSPIRO PYRIDINE DERIVATIVES

BACKGROUND OF THE INVENTION

The production of a spiro[cyclopentane]quinolinedione is described in Chem. Pharm. Bull., 17, 1290 (1969). Several additional spiroquinoline diones are disclosed in Bull. Soc. Chim. Fr., 364 (1968). The references do not describe pharmaceutical uses for these compounds.

The compounds employed in the present application are disclosed in European published application No. 84 11 4974 published June 19, 1985. That application does not disclose the compounds for use in the treatment of hyperproliferative skin disease.

SUMMARY OF THE INVENTION

This invention is a method of treating hyperproliferative skin disease in a mammal comprising administering to said mammal an anti-hyperproliferative skin disease effective amount of a compound having the structural formula I:

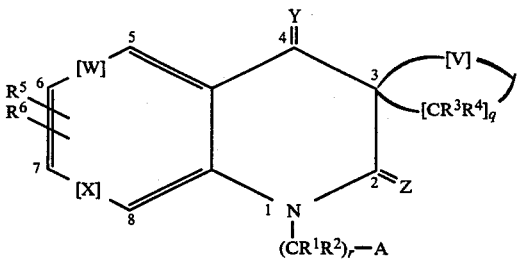

wherein
- W and X may be the same or different and represent CH or N and are at any of the ring positions 5, 6, 7 or 8;
- Y and Z may be the same or different and are O or S;
- $R^5$ and $R^6$ may be the same or different and are hydrogen, alkyl having from 1 to 6 carbon atoms, halogen, nitro, alkoxy having from 1 to 6 carbon atoms, trifluoromethyl, alkylthio having 1 to 6 carbon atoms, or cyano;
- $R^1$, $R^2$, $R^3$ and $R^4$ are independently hydrogen, alkyl having 1 to 6 carbon atoms, hydroxy, $CH_2OH$, $CO_2R_7$, wherein $R^7$ is hydrogen or alkyl having 1 to 6 carbon atoms; provided that only one group on any carbon atom is —OH and such carbon atom is not adjacent to a heteroatom;
- V is oxygen, $S(O)_n$ {wherein n is 0, 1 or 2}, or N—$R^8$ {wherein $R^8$ is hydrogen, alkyl having from 1 to 6 carbon atoms, carboxylic acyl having from 2 to 7 carbon atoms, sulfonylalkyl having from 1 to 6 carbon atoms, carboalkoxy having from 2 to 7 carbon atoms, $CONH_2$, phenyl, pyridinyl of which the last two may be substituted with up to three of any of the following substituents, Q: hydroxy, alkyl having from 1 to 6 carbon atoms, halogen, nitro, alkoxy having from 1 to 6 carbon atoms, trifluoromethyl, cyano, cycloalkyl having from 3 to 7 carbon atoms, alkenyloxy having from 3 to 6 carbon atoms, alkynyloxy having from 3 to 6 carbon atoms, $S(O)_n$—$R^a$ (wherein n is as defined above and $R^a$ is alkyl having from 1 to 6 carbon atoms), $NHSO_2R^a$ (wherein $R^a$ is defined herein above), $NHSO_2CF_3$, $NHCOCF_3$, $SO_2NH_2$, $COR^b$ (wherein $R^b$ is OH, $NH_2$, NH—$R^a$ or $OR^a$ wherein $R^a$ is as defined above), O—B—$COR^b$ (wherein B is alkanediyl having from 1 to 4 carbon atoms and $R^b$ is as defined above), or $NHCOR^c$ (wherein $R^c$ is hydrogen, alkyl having from 1 to 6 carbon atoms), $COR^d$ (wherein $R^d$ is hydroxy or alkoxy having from 1 to 6 carbon atoms), alkoxy having from 1 to 6 carbon atoms, or $NHR^e$ (wherein $R^e$ is hydrogen or alkyl having 1 to 6 carbon atoms))};
- r is 0, 1 or 2;
- q is an integer of from 2 to 6; and
- A is phenyl, naphthylenyl, indenyl, indanyl, pyridinyl, pyrimidinyl, pyrazinyl, furanyl, thienyl, imidazolyl, thiazolyl or oxazolyl any of which may be substituted with up to three substituents, Q as defined herein.

A preferred subgenus of compounds used in the treatment of hyperproliferative skin disease is that wherein Y and Z are both oxygen.

An additional preferred subgenus of compounds used in the treatment of hyperproliferative skin disease is represented by the structural formula II:

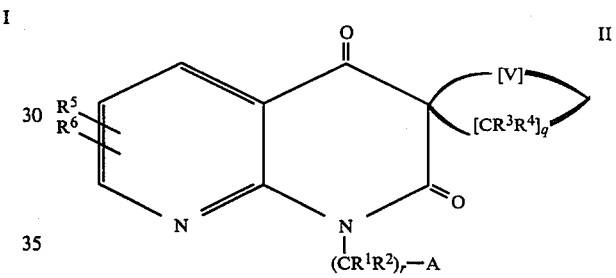

wherein $R^1$, $R^2$, $R^3$, $R^4$, $R^5$, $R^6$, A, r and q are defined herein.

An additional preferred subgenus of compounds used in the treatment of hyperproliferative skin disease is represented by the structural formula III:

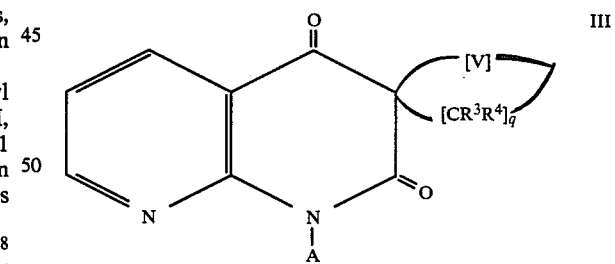

wherein $R^3$, $R^4$, V, A, and q are defined herein.

A further additional preferred subgenus of compounds used in the treatment of hyperproliferative skin disease is represented by the structural formula III wherein $R^3$, $R^4$, A and q are as defined herein and V is oxygen.

The invention further encompasses the topical administration of a pharmaceutical composition to said mammal, said pharmaceutical composition comprising a chemical compound of structural formula I in combination with a topical pharmaceutically acceptable carrier.

The invention further encompasses the topical administration of a compound of structural formula I.

The compounds of formula I as defined above are disclosed in U.S. application Ser. No. 641,076, filed Aug. 15, 1984, the disclosure of which is incorporated herein by reference.

DESCRIPTION OF THE INVENTION

The compounds of the invention may be prepared from a properly substituted compound having the structural formula IV

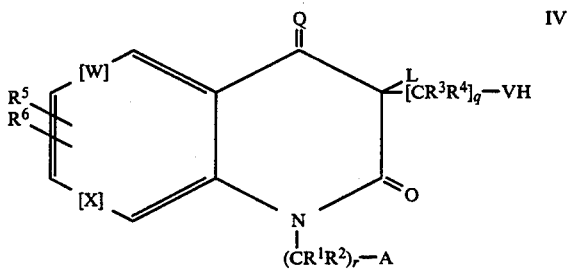

wherein W, X, $R^1$, $R^2$, $R^3$, $R^4$, $R^5$ $R^6$, V, A, r and q are defined herein, and L is a substituent known to those skilled in the art as a "leaving group."

Treatment of compound IV with an organic base such as triethylamine or 1,8-diazabicyclo [5.4.0] undec-7-ene, DBU [Angew. Chem., Internat. Ed., 6 76 (1967)] in a nonreactive solvent such as chloroform will produce the compounds of the invention having structural formula I, wherein Y and Z are both oxygen.

For purposes of describing the compounds used herein, a "leaving group" is defined as a substituent which may be displaced and carry a negative charge. Examples of such substituents are the bromide and iodide anions. The preferred leaving group is the bromide anion.

Compounds having structural formula IV wherein L is bromine and VH is hydroxy may be prepared by treatment of the corresponding non-brominated compounds with a solution of bromine in chloroform. Other compounds having structural formula IV wherein the leaving group substituent L is iodine and VH is hydroxy may be prepared by methods known to those of skill in the art.

The compounds having structural formula IV without the leaving group substituent L may be prepared by known methods from known starting materials. Such methods are described, for example, in preparative examples 1, 2, 4 and 6 herein.

Exemplary of such starting materials for preparing compounds having structural formula IV without leaving group substituent L are 2-anilino nicotinic acids which may be prepared, for example, as described in U.S. Pat. No. Re. 26,655; and 2-phenylamino-3-pyrazine carboxylate esters which may be prepared substantially as exemplified herein starting with a 2-amino-3-pyrazine carboxylate ester. 2-Anilino-3-pyrazine carboxylic acid is a known compound, C. A., 75, 20154e (1971), which may be esterified by standard procedures.

The compounds having structural formula I wherein Y and/or Z are oxygen may be converted to the corresponding compounds wherein Y and/or Z are sulfur by known methods. For example treatment with Lawesson's Reagent [2,4-bis(4-methoxyphenyl)-1,3-dithia-2,4-diphosphetane-2,4-disulfide] in hot toluene will effect this conversion.

When utilized herein and in the appended claims the below listed terms, unless specified otherwise, are defined as follows:

halogen—fluorine, chlorine, bromine and iodine;
alkyl and alkoxy—comprised of straight and branched carbon chains containing from 1 to 6 carbon atoms;
alkanediyl—comprised of divalent, straight or branched carbon chains containing from 1 to 4 carbon atoms;
alkenyloxy—comprised of straight and branched carbon chains containing from 3 to 6 carbon atoms and comprising a carbon to carbon double bond; and
alkynyloxy'comprised of straight and branched carbon chains containing from 3 to 6 carbon atoms and comprising a carbon to carbon triple bond.

The compounds of the invention include a $-(CR^1R^2)_r-$ substituent wherein the $R^1$ and $R^2$ groups may vary independently. Thus, for example, when r equals 2 the following patterns of substitution (wherein hydrogen and $CH_3$ are used to represent any substituent, $R^1$ or $R^2$,) are contemplated: $-C(CH_3)_2CH_2-$, $-CH_2C(CH_3)_2-$, $-CH_2CH(CH_3)-$, $-CH(CH_3)CH_2-$, $-(C(CH_3)H)_2-$ and the like. In addition when r equals 2, substituents such as $-C(CH_3)_2CH(C_2H_5)-$, $-CH(CH_3)CH(C_2H_5)-$, $-CH(i-C_3H_7)CH(C_2H_5)-$ are also contemplated.

It is recognized that due to problems of stability, there are limitations involving the $R^1$ and $R^2$ groups. One limitation is that neither the $R^1$ nor $R^2$ group can be an hydroxy group attached to the carbon atom alpha to the ring nitrogen. Another limitation is that the $R^1$ and $R^2$ groups cannot both be hydroxy groups.

The compounds of the invention include $-(CR^3R^4)_q-$ substituents wherein the $R^3$ and $R^4$ groups may vary independently. Thus, for example, when q equals 2 the following patterns of substitution (wherein hydrogen and $CH_3$ are used to represent any substituent, $R^3$ or $R^4$,) are contemplated: $-C(CH_3)_2CH_2-$, $-CH_2C(CH_3)_2-$, $-CH_2CH(CH_3)-$, $CH(CH_3)CH_2-$, $-(C(CH_3)H)_2-$, and the like. In addition when q equals 2, substitutents such as $-C(CH_3)_2CH(C_2H_5)-$, $-CH(CH_3)CH(C_2H_5)-$, $-CH(i-C_3H_7)CH(C_2H_5)-$ are also contemplated.

It is further recognized that due to problems of stability there are limitations involving the $R^3$ and $R^4$ groups. One limitation is that neither the $R^3$ nor $R^4$ group can be a hydroxy group attached to the carbon atom alpha to the ring heteroatom. Another limitation is that the $R^3$ and $R^4$ groups cannot both be hydroxy groups.

Certain compounds described and utilized herein may exist in isomeric forms. The invention contemplates all such isomers both in pure form and in admixture, including racemic mixtures.

In structural formulas I, II and III herein, substituent V which represents the hetero atom in the spiro ring is attached directly to the spiro carbon atom, i.e. the carbon atom identified as number 3 in structural formula I.

The compounds of formula I can exist in unsolvated as well as solvated forms, including hydrated forms. In general, the solvated forms, with pharmaceutically acceptable solvents such as water, ethanol and the like are equivalent to the unsolvated forms for purposes of the invention.

A compound of formula I may be utilized to treat hyperoroliferative skin disease in a mammal. As used herein, "hyperproliferative skin disease" means any condition a symptom of which is accelerated skin cell production, flaking, scales or papular lesions. Representative examples of hyperproliferative skin diseases include osoriasis, eczema, dandruff and the like. Effectiveness of the compounds of formula I for the treatment of hyperproliferative skin disease may be demonstrated by the Arachidonic Acid Mouse Ear Test, as described in detail below. The Arachidonic Acid Mouse Ear Test is a recognized model for assessing the effectiveness of compounds for the treatment of hyperproliferative skin disease.

Arachidonic Acid Mouse Ear Test, Materials and Methods

Charles River, female, CD, (SD) BR mice, 6 weeks old, are caged 8/group and allowed to acclimate 1-3 weeks prior to use.

Arachidonic acid (AA) is dissolved in reagent grade acetone (2 mg/0.01 ml) and stored at $-20°$ C. for a maximum of 1 week prior to use. Inflammatory reactions are induced by applying 10 $\mu$l of AA to both surfaces of one ear (4 mg total).

Test drugs are dissolved in either reagent grade acetone or acueous ethanol (only if insoluble in acetone) at the same doses selected by Opas et al., *Fed. Proc.* 43, Abstract 2983, P. 1927 (1984) and Young et al., *J. Invest. Dermatol.* 82, pp. 367-371 (1984). These doses are employed to ensure maximum responses and to overcome any difference in topical absorption which could occur with any drug applied in an aqueous ethanol vehicle. The test drug is applied 30 minutes prior to challenge with AA.

The severity of the skin reaction is measured as a function of increased ear weight. A 6 mm punch biopsy is removed 1 hour after AA challenge and weighed to the nearest 0.1 mg. Mean $\pm$ standard error and all possible comparisons are made via Duncan's Multiple Range Statistic.

A representative example of the compounds of formula I and effectiveness for the treatment of hyperproliferative skin disease is shown below in Table 1.

TABLE 1

ADMINISTRATION OF
1-PHENYL-3',4',5',6'-TETRAHYDRO-SPIRO[1,8-NAPHTHYRIDINE-3,2'-(2H)PYRAN]-2,4-DIONE

| Dose (mg/ear) | Tissue Wt. (g) | % Inhibition |
|---|---|---|
| 1.0 | 2.27 ± 0.29 | 67% |
| 0.5 | 4.39 ± 0.62 | 37% |
| 0.25 | 4.97 ± 0.70 | 28% |
| 0.125 | 4.86 ± 0.39 | 30% |

As a result of the administration of a compound of formula I, a remission of the symptoms of hyperproliferative skin disease can be expected. Thus, for example, one affected by psoriasis can expect a decrease in scaling, erythema, size of plaques, pruritus and other symptoms associated with psoriasis. The dosage of medicament and the length of time required for successfully treating each individual psoriatic patient may vary, but those skilled in the art of medicine will be able to recognize these variations and adjust the course of therapy accordingly.

When administered for the treatment of hyperproliferative skin disease, the compounds may be administered topically, orally, rectally or parenterally. When administered topically, the amount of compound administered varies widely with the amount of skin being treated, as well as with the concentration of active ingredient applied to the affected area. When administered orally, the compounds of formula I are effective for the treatment of hyperproliferative skin disease at doses ranging from about 0.1 mg to about 100 mg, which may be administered in divided doses. When administered rectally, the compounds of formula I may be administered in doses ranging from about 0.1 mg to about 1000 mg. When administered parenterally, the compounds of formula I are effective for the treatment of hyperproliferative skin disease in doses ranging from about 0.1 mg/kg body weight to about 10 mg/kg body weight which may be administered in divided doses.

Included within the invention are preparations for topical application to the skin whereby the compounds having structural formula I are effective in the treatment and control of skin diseases characterized by rapid rates of cell proliferation and/or abnormal cell proliferation, e.g. psoriasis.

In a preferred method of carrying out the invention, a pharmaceutical formulation comprising a compound of formula I together with a non-toxic, pharmaceutically acceptable topical carrier, usually in concentrations in the range of from about 0.001 percent to about 10 percent, preferably from about 0.1 percent to about 5 percent, is applied several times daily to the affected skin until the condition has improved. Topical applications may then be continued at less frequent intervals (e.g. once a day) to control mitosis in order to prevent return of severe disease conditions.

The compounds of formula I may also be used systemically for the treatment of hyperproliferative skin diseases, e.g., orally or parenterally. A dosage range of from about 5 mg/kg to 50 mg/kg, p.o., in divided doses taken at about 4 to 12 hour intervals is recommended. When administered parenterally, e.g. intra venously, the compounds may be administered at a dosage range of about 0.05-5 mg/kg of body weight in single or multiple daily doses.

For preparing pharmaceutical compositions from the compounds described by this invention, inert, pharmaceutically acceptable carriers can be either solid or liquid. Solid form preparations include powders, tablets, dispersible granules, capsules, cachets and suppositories. A solid carrier can be one or more substances which may also act as diluents, flavoring agents, solubilizers, lubricants, suspending agents, binders or tablet disintegrating agents; it can also be an encapsulating material. In powders, the carrier is a finely divided solid which is in admixture with the finely divided active compound. In the tablet the active compound is mixed with carrier having the necessary binding properties in suitable proportions and compacted in the shape and size desired. The powders and tablets are preferably comprised of from 5 or 10 to about 70 percent active ingredient on a weight/weight basis. Suitable solid carriers include magnesium carbonate, magnesium stearate, talc, sugar, lactose, pectin, dextrin, starch, gelatin, tragacanth, methylcellulose, sodium carboxymethylcellulose, a low melting wax, cocoa butter and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets and capsules can be used as solid dosage forms suitable for oral administration.

A compound of formula I may be conveniently applied in a liquid solvent, preferably in a water-miscible liquid carrier made up of hydrophilic liquids having a high solvating action, e.g., a solution which comprises, for example, propylene glycol and polyethylene glycol. Alternatively, a compound may be applied in dry form, such as a powder. Other forms in which the compounds may be used topically include creams, lotions, aerosols, dusts and ointments which are prepared by combining a compound of formula I with conventional pharmaceutical diluents and carriers commonly used in topical dry, liquid, cream and aerosol formulations.

The ointments and creams may, for example, be formulated with an aqueous oily base with the addition of suitable thickening and/or gelling agents. Such bases may thus, for example, include water and/or oil such as liquid paraffin or vegatable oil, such as peanut oil or castor oil. Thickening agents which may be used according to the nature of the base include soft paraffin, aluminum stearate, cetostearyl alcohol, propylene glycol, polyethylene glycols, woolfat, hydrogenated lanolin, beeswax, etc.

Lotions may be formulated with an aqueous or oily base and will, in general, also include one or more of the following, namely, stabilizing agents, emulsifying agents, dispensing agents, suspending agents, thickening agents, coloring agents, perfumes and the like.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Liquid form preparations include solutions, suspensions and emulsions. As an example may be mentioned water or water-propylene glycol solutions for parenteral injection. Liquid preparations can also be formulated in solution in aqueous polyethylene glycol solution. Aqueous solutions suitable for oral use can be prepared by adding the active component in water and adding suitable colorants, flavors, stabilizing, sweetening, solubilizing and thickening agents as desired. Aqueous suspensions suitable for oral use can be made by dispersing the finely divided active component in water with viscous material, i.e., natural or synthetic gums, resins, methylcellulose, sodium carboxymethylcellulose and other well-known suspending agents.

Also included are solid form preparations which are intended to be converted, shortly before use, to liquid form preparations for topical, oral or parenteral administration. Such liquid forms include solutions, suspensions and emulsions. These particular solid form preparations are most conveniently provided in unit dose form and as such are used to provide a single liquid dosage unit. Alternately, sufficient solid may be provided so that after conversion to liquid form, multiple individual liquid doses may be obtained by measuring predetermined volumes of the liquid form preparation as with a syringe, teaspoon or other volumetric container. When multiple liquid doses are so prepared, it is preferred to maintain the unused portion of said liquid doses at low temperature (i.e., under refrigeration) in order to retard possible decomposition. The solid form preparations intended to be converted to liquid form may contain, in addition to the active material, flavorants, colorants, stabilizers, buffers, artificial and natural sweeteners, dispersants, thickeners, solubilizing agents and the like. The solvent utilized for preparing the liquid form preparation may be water, isotonic water, ethanol, glycerine, propylene glycol and the like as well as mixtures thereof. Naturally, the solvent utilized will be chosen with regard to the route of administration, for example, liquid preparations containing large amounts of ethanol are not suitable for parenteral use.

Preferably, the pharmaceutical preparation for oral or parenteral use is in unit dosage form. In such form, the preparation is subdivided into unit doses containing appropriate quantities of the active component. The unit dosage form can be a packaged preparation, the package containing discrete quantities of preparation, for example, packeted tablets, capsules and powders in vials or ampoules. The unit dosage form can also be a capsule, cachet or tablet itself or it can be the appropriate number of any of these in packaged form.

The quantity of active compound in a unit dose of preparation may be varied or adjusted from about 1 mg to 100 mg according to the particular application and the potency of the active ingredient. The compositions can, if desired, also contain other therapeutic agents.

The dosages may be varied depending upon the requirements of the patient, the severity of the condition being treated and the particular compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

PREPARATIVE EXAMPLE 1

4-Hydroxy-3-(4-hydroxybutyl)-1-phenyl-1,8-naphthyridin-2(1H)-one

A mixture of methyl 2-phenylamino-nicotinate (100 g.), epsilon-caprolactone (1000 g.) and potassium t-butoxide (200 g.) was stirred at room temperature, in a nitrogen atmosphere, for ½ hr. It was heated at 45° C. for 1 hr. When at 85° C. for 2 hrs. and finally at 105° C. for 3 hr.

The hot mixture was poured carefully into 8 L of 5% KOH solution and was stirred overnight.

The mixture was extracted with 2 L of ether and the aqueous phase was retained. It was extracted again with a fresh 2 L of ether. The clear aqueous phase was adjusted to pH 4.5 with conc. HCl to yield a white solid which was filtered off, washed with water and dried to yield 4-hydroxy-3-(4-hydroxybutyl)-1-phenyl-1,8-naphthyridin-2(1H)-one, m.p. 205.5°-206.5° C. (from isopropanol).

By substituting the relevant ester and lactone in this preparative example intermediates to other compounds of the invention may be prepared.

PREPARATIVE EXAMPLE 2

4-Hydroxy-3-(3-hydroxypropyl)-1-phenyl-1,8-naphthyridin-2(1H)one

Methyl 2-phenylamino-nicotinate (25 g.) was dissolved in delta-valerolactone (240 g.) with stirring in an atmosphere of nitrogen. To the resulting solution was added potassium t-butoxide (50 g.) and the mixture was stirred at room temperature for ½ hr. It was then heated to 100° C. for 3 hr. after which time it was poured into 1L of 5% NaOH solution and stirred overnight.

The mixture was extracted (2×) with 1 L of ether then the aqueous layer was adjusted to pH 4.5 with conc. HCl. The solid which separated was filtered off, washed with water and dried to yield 4-hydroxy-3-(3-hydroxypropyl)-1-phenyl-1,8-naphthyridin-2(1H)-one, m.p. 218°–220° C.

By utilizing the correspondingly substituted starting materials in the procedures of preparative examples 1 or 2, the following compounds were obtained:

1-(4-chlorophenyl)-4-hydroxy-3-(3-hydroxypropyl)-1,8-naphthyridin-2(1H)one, m.p. 249.5°–251° C.;
4-hydroxy-3-(3-hydroxypropyl)-1-(4-methylphenyl)-1,8-naphthyridin-2(1H)one, m.p. 227°–228° C.;
4-hydroxy-3-(3-hydroxypropyl)-1-(4-methoxyphenyl)-1,8-naphthyridin-2(1H)one, m.p. 229°–231° C.;
1-(3,4-dichlorophenyl)-4-hydroxy-3-(3-hydroxypropyl)-1,8-naphthyridin-2(1H)one, m.p. 230°–232° C.;
1-(4-chlorophenyl)-4-hydroxy-3-(4-hydroxybutyl)-1,8-naphthyridin-2(1H)one, m.p. 238°–240° C.;
4-hydroxy-3-(4-hydroxybutyl)-1-(4-methylphenyl)-1,8-naphthyridin-2(1H)one, m.p. 186°–188° C.;
4-hydroxy-3-(4-hydroxybutyl)-1-(4-methoxyphenyl)-1,8-naphthyridin-2(1H)one, m.p. 237°–239° C.;
1-(3,4-dichlorophenyl)-4-hydroxy-3-(4-hydroxybutyl)-1,8-naphthyridin-2(1H)one, m.p. 188°–190° C.;
1-(3-chlorophenyl)-4-hydroxy-3-(4-hydroxybutyl)-1,8-naphthyridin-2-(1H)one, m.p. 176°–178° C.;
4-hydroxy-3-(4-hydroxybutyl)-1-(3-methoxyphenyl)-[1,8]-naphthyridin-2(1H)-one, m.p. 217°–219° C.;
4-hydroxy-3-(4-hydroxybutyl)-1-phenyl-quinolin-2(1H)-one, m.p. 156.5°–158° C.

PREPARATIVE EXAMPLE 3

Ethyl-5-(4-hydroxy-2-oxo-1-phenyl-1H-[1,8]naphthyridin-3-yl)pentanoate

Methyl 2-phenylaminonicotinate (8.5 g.) was dissolved with stirring in diethyl pimelate (80 ml.) in an atmosphere of nitrogen. To the mixture was added potassium t-butoxide (13 g.) and the mixture was stirred at room temperature for 1 hr. It was then heated to 135°–140° C. for 6 hours after which time it was poured into water. The aqueous layer was extracted with methylene chloride and then adjusted to pH 4.5 with conc. HCl. Solid sodium chloride was added after which the solid was filtered off, washed with water and dried, m.p. 168°–169° C.

By substituting diethyl suberate for diethylpimelate in the above procedure; ethyl 6-(4-hydroxy-2-oxo-1-phenyl-1H-[1,8]naphthyridin-3-yl)-hexanoate, m.p. 167°–168° C. was obtained.

PREPARATIVE EXAMPLE 4

4-Hydroxy-3-(5-hydroxypentyl)-1-phenyl-1,8-naphthyridin-2(1H)one

To a suspension of ethyl 5-(4-hydroxy-2-oxo-1-phenyl-1H-[1,8]-naphthyridin-3-yl)pentanoate (1 g.) (prepared as in preparative example 3) in dry dioxane (50 ml.) in an atmosphere of nitrogen is added lithium borohydride (0.34 g.). The mixture is stirred at room temperature for 20 min. then it is heated to 60° C. for 16 hrs.

The product is poured into water, adjusted to pH 4.5 with acetic acid and the resulting solid is filtered off. The solid is washed with water and dried to yield 4-hydroxy-3-(5-hydroxypentyl)-1-phenyl-1,8-naphthyridin-2-(1H)-one.

PREPARATIVE EXAMPLE 5

Methyl-2-phenylamino-3-pyrazine carboxylate (A) Methyl 2-bromo-3-pyrazine carboxylate To a stirred mixture of 12.7 g. of methyl 2-amino pyrazine carboxylate and 47 ml. of 48% hydrobromic acid there was added, dropwise, 12.6 ml. of bromine keeping the temperature at 0°. A solution of 14.4 g. of sodium nitrite in 60 ml. of water was then added, dropwise, at 0° and the reaction mixture stirred for 15 minutes. The reaction mixture was basified to pH 8 with sodium bicarbonate and extracted with ethyl acetate and again with chloroform. The organic layers were dried over magnesium sulfate, filtered and concentrated to a yellow oil. Recrystallization from ether-hexane yielded the product, m.p. 43°–45° C.

(B) Methyl 2-phenylamino-3-pyrazine carboxylate

A mixture of 9.5 g. of methyl 2-bromo-3-pyrazine carboxylate, 8.2 g. of aniline, 0.5 g. of p-toluene sulfonic acid and 100 ml. of water was stirred and refluxed for two hours. The reaction mixture was poured on ice, extracted with ethyl acetate, the organic extracts were dried and concentrated to yield an oil. The crude residue was eluted on a silica gel column with ethyl acetate-hexane (1:2) yielding the product of this example as a yellow solid, m.p. 72°–75° C.

PREPARATIVE EXAMPLE 6

3-(2-Hydroxyethyl)-4-hydroxy-1-phenyl-1,8-naphthyridin-2(1H)one

To a solution of 6.8 g. of methyl 2-phenylamino-3-pyridine carboxylate in 60 ml. of gamma-butyrolactone there was added, under nitrogen, 13.4 g. of potassium tertiary butoxide. The reaction mixture was heated and stirred for one hour at 95° C., poured on ice and stirred overnight. The mixture was extracted with ether, the aqueous layer acidified with acetic acid to pH 4.5 and the product was collected by filtration. Recrystallization from chloroform, acetone, isopropanol yielded the product of this example as a colorless solid; m.p. 235°–236° C.

EXAMPLE 1

1-Phenyl-3',4',5',6'-tetrahydro-spiro-[1,8-naphthyridine-3,2'-(2H)pyran]- 2,4-dione A suspension of 4-Hydroxy-3-(4-hydroxybutyl)-1-phenyl-(1,8)-naphthyridin-2(1H)-one (2 g.) in chloroform was stirred in an ice-bath. A solution of bromine (1 g.) in chloroform was added dropwise and the mixture was stirred overnight at room temperature. To this mixture was added a solution of 1,8-diazabicyclo[5.4.0]undec-7-ene (2 g) in chloroform at room temperature. After about ¾ hr. water was added and the pH was adjusted to be slightly acidic. The chloroform layer was separated and washed with saturated NaCl solution. The solution was dried and evaporated to a solid which was washed with ethanol/water and dried to yield 1-phenyl-3',4', 5', 6'-tetrahydro-spiro[1,8-naphthyridine-3,2'-(2H) pyran]-2,4-dione, m.p. 213°–215° C.

EXAMPLE 2

1-(3-Methoxyphenyl)-3', 4', 5', 6'-tetrahydrospiro[1,8-naphthyridine-3,2'-(2H)pyran]-2,4-dione To a suspension of 4-Hydroxy--(4-hydroxybutyl)-1-(3-methoxyphenyl)(1,8)-naphthyridin-2(1H)-one (1 g.) in methylene chloride (10 ml), in an ice-acetone bath was added a solution of bromine (0.5 g.) in methylene chloride (5 ml.) over a period of 15 min. The resulting yellow-orange suspension was stirred overnight at room temperature. To the resulting clear yellow solution was added a solution of 1,8-diazabicyclo[5.4.0]undec-7-ene (1 g.), in methylene chloride (5 ml.) during 5 mins. The mixture was stirred at room temperature for 3 hrs. after which time water (5 ml) was added. The organic layer was separated, dried and evaporated. To the residue was added 50% aqueous ethanol (10 ml.) and after some time the solid was filtered off and recrystallized from isopropanol to yield 1-(3-methoxyphenyl)-3′, 4′,5′, 6′-tetrahydrospiro[1,8-naphthyridine-3,2′-(2 H)pyran]-2, 4-dione, m.p. 181°–183° C.

By utilizing the appropriately substituted starting materials in the above-described procedure, the following products were obtained:

4,5-dihydro-1′-phenyl-spiro [furan-2(3H), 3′(2′H) (1,8) naphthyridine]-2′, 4′(1′H)-dione, m.p. 241.5°–243° C.; 1-phenyl-spiro(1,8-naphthyridine-3,2′-oxetane)-2, 4-dione, m.p. 233°–235.5° C.; and 1-(3-chlorophenyl)-3′, 4′, 5′, 6′,-tetrahydrospiro[1,8-naphthuridine-3, 2′(2H) pyran]-2,4-dione, m.p. 158.5°–160° C.

EXAMPLE 3

1′-Ethoxycarbonyl-1-phenylspiro[1,8-naphthyridine 3,2′-piperidine]-2,4-dione (A)

N,2-Bis(ethoxycarbonyl)-2-(3-[2-chloronicotinoyl])-piperidine

A slight excess of 1M-lithium bis(trimethylsilyl)amide in tetrahydrofuran (THF) is cooled in a nitrogen atmosphere to below −60° C. To this is added a solution of ethyl N-ethoxycarbonyl pipecolinate (0.11 M) in dry THF, dropwise.

Allow to stand for 2 hr. Then add a solution of ethyl 2-chloronicotinate (0.1 M) in dry THF, dropwise.

Allow to stand at −70° C. for at least 4 hrs. Then warm gradually to room temperature. When no starting material remains, add acetic acid and water, and evaporate off the THF.

Isolate the product by extraction and purify by column chromatography.

(B)

N-Ethoxycarbonyl-2-(3-[2-chloro-nicotinoyl])-pipecolinoyl anilide

Carefully hydrolyze the product from part A using excess dilute NaOH in H₂)/EtOH. Follow by thin layer chromatography (TLC). When no starting material remains, adjust the pH to ca 9 with dil HCl and evaporate to low volume under reduced pressure. To the residue suspended in benzene, add an excess of oxalyl chloride, and warm the mixture until a reaction occurs.

When the reaction is complete evaporate off as much solvent and excess reagent as possible. Then add aniline (2.2 equivs.) in dry THF. Warm to complete the reaction. Then isolate the product by adding water and acetic acid, evaporating off the THF and extracting into CH₂Cl₂. The product is purified by column chromatography.

(C)

1′-Ethoxycarbonyl-1-phenyl-spiro(1,8-naphthyridine-3,2′-piperidine]-2,4-dione

To a slight excess of 1M-lithium bis(trimethylsilyl)amide in THF, under nitrogen, at −70° C., is added the product from part B, in dry THF, dropwise. After standing for 2 hr. at −70° C. the mixture is allowed to warm gradually in ca. 20° C. steps to room temperature. The reaction is followed by TLC at each step. When the reaction is complete, the product is isolated by addition of acetic acid and water. Removal of the THF, and extraction into CH₂Cl₂ is performed, and the product is purified by column chromatography.

Removal of the carbamate protecting group and subsequent modification of the resulting secondary amine are implemented by standard means well known to one skilled in the art.

The following formulations exemplify some of the dosage forms in which the compounds of the invention may be employed. In each, the active ingredient is the 1-phenyl-3′,4′,5′,6′-tetrahydro-spiro[1,8-naphthyridin-3,2′-(2H)pyran]-2,4-dione and is referred to as "active compound". However, it is to be understood that any other compound of structural formula I could be substituted. Consequently, the scope of the formulation examples is not to be limited thereby.

FORMULATIONS

| Formulation I: Ointment | |
|---|---|
| Formula | mg/g |
| Active Compound | 1.0–20.0 |
| Benzyl Alcohol, NF | 10.0 |
| Mineral Oil, USP | 50.0 |
| White Petrolatum, USP to make | 1.0 g |

Procedure

Mix and heat to 65° C., a weighted quantity of white petrolatum, mineral oil, benzyl alcohol, and cool to 50°–55° C. with stirring. Disperse active compound in a portion of the mineral oil and then add to the above mixture with stirring. Cool to room temperature.

| Formulation II: Cream | |
|---|---|
| Formula | mg/g |
| Active Compound | 1.0–20.0 |
| Stearic Acid, USP | 60.0 |
| Glyceryl Monostearate | 100.0 |
| Propylene Glycol, USP | 50.0 |
| Polyethylene Sorbitan Monopalmitate | 50.0 |
| Sorbitol Solution, USP | 30.0 |
| Benzyl Alcohol, NF | 10.0 |
| Purified Water, USP to make | 1.0 g |

Procedure

Heat the stearic acid, glyceryl monostearate and polyethylene sorbitan monopalmitate to 70° C. In a separate vessel, dissolve sorbital solution, benzyl alcohol, water, and half quantity of propylene glycol and heat to 70° C. Add the aqueous phase to oil phase with high speed lightning stirring. Dissolve the active compound in remaining quantity of propylene glycol and add to the above emulsion when the temperature of emulsion is 37°–40° C. Mix uniformly with stirring and cool to room temperature.

| Formulation III: Gel | |
|---|---|
| Formula | mg./g |
| Active Compound | 1.0–20.0 |
| Propylene Glycol, USP | 300.0 |
| Butylated Hydroxytoluene | 5.0 |
| Carbomer 940 | 5.0 |
| Sodium Hydroxide (added as a 1% w/w solution in proplyene glycol) | 0.7 |
| Polyethylene Glycol 400, USP | 669.3–688. |

Procedure

Prepare a 1% solution of the sodium hydroxide in propylene glycol and hold. Add approximately one-half the remaining propylene glycol, and the polyethylene glycol 400 to a suitable vessel and mix. Dissolve the butylated hydroxytoluene in this mixture. Disperse the carbomer 940 in the above mixture with vigorous agitation. Add the solution of sodium hydroxide with high speed agitation to bring pH up to 7 and recirculation until a thick gel forms. Dissolve the active compound in the remaining propylene glycol and add to the gel slowly as the gel is continuously recirculated.

| Formulation IV: Lotion | |
|---|---|
| Formula | mg/g |
| Active Compound | 1.0–20.0 |
| Carbomer 940 | 3.0 |
| Sodium hydroxide (charged as 4% w/w aqueous solution) | 0.05 |
| Isopropyl Alcohol | 40.00 |
| Purified Water, USP to make | 1.0 g |

Procedure

Prepare a 4% solution of sodium hydroxide in water. Heat the purified water to 60° C. Add carbomer 940 and mix at high speed until dispersed. Cool the above mixture to room temperature and slowly charge sodium hydroxide until uniform. Add 80% of isopropyl alcohol to the above with mixing. Dissolve the active compound in remaining isopropanol. Add this to the mixture with stirring. Adjust pH to 5.0 to 5.5 with sodium hydroxide, if necessary.

| Formulation V: Topical Aerosol | |
|---|---|
| Formula | mg/g |
| Active Compound | 1.0–20.0 |
| Caprylic/Capric Triglyceride | 50.00 |
| Mineral Oil | 20.00 |
| Specially Denatured Alcohol | 150.00 |
| Hydrocarbon Aerosol Propellant q.s. ad. | 1.0 g |

Procedure

Add and mix the caprylic/capric triglyceride mineral oil and specially denatured alcohol in a suitable compounding tank. Add the active compound drug and continue mixing until the active compound is dissolved or dispersed uniformily. Fill the concentrate into cans and then fill the required amount of hydrocarbon aerosol propellant.

I claim:

1. A method of treating hyperproliferative skin disease in a mammal comprising administering to said mammal an anti-hyperproliferative skin disease effective amount of a compound of formula I

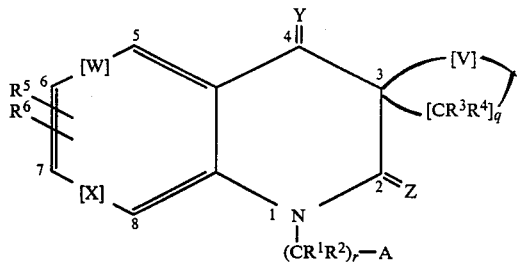

wherein:

W and X may be the same or different and represent CH or N;

Y and Z may be the same or different and are O or S;

$R^5$ and $R^6$ may be the same or different and are hydrogen, alkyl having from 1 to 6 carbon atoms, halogen, nitro, alkoxy having from 1 to 6 carbon atoms trifluoromethyl, alkylthio having 1 to 6 carbon atoms or cyano;

$R^1$, $R^2$, $R^3$ and $R^4$ are independently hydrogen, alkyl having 1 to 6 carbon atoms, $CH_2OH$, $CO_2R^7$ {wherein $R^7$ is hydrogen or alkyl having 1 to 6 carbon atoms} or hydroxy, provided that only one group on any carbon atom is —OH and that such carbon atom is not adjacent to a heteroatom;

V is oxygen, $S(O)_n$ {wherein n is 0, 1 or 2}, or N—$R^8$ {wherein $R^8$ is hydrogen, alkyl having from 1 to 6 carbon atoms, carboxylic acyl having from 2 to 7 carbon atoms, sulfonylalkyl having from 1 to 6 carbon atoms, carboalkoxy having from 2 to 7 carbon atoms, $CONH_2$, phenyl, pyridinyl of which the last two may be substituted with up to three of any of the following substituents, Q: hvdroxy, alkyl having from 1 to 6 carbon atoms, halogen, nitro, alkoxy having from 1 to 6 carbon atoms, trifluoromethyl, cyano, cycloalkyl having from 3 to 7 carbon atoms, alkenyloxy having from 3 to 6 carbon atoms, alkynyloxy having from 3 to 6 carbon atoms, $S(O)_n$—$R^a$ (wherein n is defined herein and $R^a$ is alkyl having from 1 to 6 carbon atoms), $NHSO_2R^a$ (wherein $R^a$ is defined herein), $NHSO_2CF_3$, $NHCOCF_3$, $SO_2NH_2$, $COR^b$ (wherein $R^b$ is OH, $NH_2$, $NHR^a$ or $OR^a$ wherein $R^a$ is defined herein), O—B—$COR^1$(wherein B is alkanediyl having from 1 to 4 carbon atoms and $R^b$ is defined herein), or $NHCOR^c$ (wherein $R^c$ is hydrogen, alkyl having from 1 to 6 carbon atoms, alkoxy having from 1 to 6 carbon atoms, $COR^d$ (wherein $R^d$ is hydroxy or alkoxy having from 1 to 6 carbon atoms) or $NHR^e$ (wherein $R^e$ is hydrogen or alkyl having 1 to 6 carbon atoms))};

r is 0, 1 or 2;

a is an integer of from 2 to 6; and

A is phenyl, naphthylenvl, indenyl, indanyl, pyridinyl, pyrimidinyl, pyrazinyl, furanyl, thienyl, imidazolyl, thiazolyl or oxazolyl any of which may be substituted with up to three substituents, Q as defined herein.

2. The method defined in claim 1 wherein Y and Z are both oxygen.

3. The method defined in claim 2 wherein r is O.

4. The method defined in claim 3 wherein $R^5$ and $R^6$ are both hydrogen.

5. The method defined in claim 4 wherein W is N and X is CH.

6. The method defined in claim 4 wherein W and X represent N at the 5- and 8- positions respectively.

7. The method defined in claim 5 wherein W is situated in the 5- or 8- position.

8. The method defined in claim 5 wherein W is situated in the 8-position.

9. The method defined in claim 8 wherein V is oxygen.

10. The method defined in claim 9 wherein q is 3, 4, or 5.

11. The method defined in claim 10 wherein up to 4 of $R^3$ and $R^4$ are alkyl having 1 to 4 carbon atoms.

12. The method defined in claim 10 wherein up to 2 of $R^3$ and $R^4$ are alkyl having 1 or 2 carbon atoms.

13. The method defined in claim 10 wherein q is 3, 4 or 5 and $R^3$ and $R^4$ are hydrogen.

14. The method defined in claim 13 wherein A is phenyl.

15. The method defined in claim 14 wherein A is phenyl substituted with one or two Q substituents.

16. The method defined in claim 1 wherein the compound is:
1-phenyl-3', 4', 5',6'-tetrahydro-spiro[1,8-naphthyridine-3,2'-(2H)pyran]-2,4-dione;
1-(3-methoxyphenyl)-3', 4', 5',6'-tetrahydrospiro[1,8-naphthyridine-3,2'-(2H)pyran]-2, 4-dione;
4, 5-dihydro-1'-phenyl-spiro[furan-2(3H), 3'(2'H) (1,8)naphthyridine]-2',4'(1'H)-dione;
1-phenyl-spiro[1,8-naphthyridine-3,2'-oxetane]-2,4-dione; or
1-(3-chlorophenyl)-3', 4', 5', 6'-tetrahydro-spiro(1,8-naphthyridine-3,2'-(2H)pyran]-2,4-dione.

17. The method defined in claim 16 wherein the compound administered is 1-phenyl-3',4', 5',6'-tetrahydrospiro[1,8-naphthyridine-3,2'-(2H)pyran]-2,4-dione.

18. The method defined in claim 1 wherein the compound is administered in the form of a pharmaceutical composition comprised of a compound of formula I in combination with a pharmaceutically acceptable carrier.

19. The method defined in claim 1 wherein the compound is administered topically.

20. The method defined in claim 18 wherein the pharmaceutical composition is in the form of a lotion.

21. The method defined in claim 18 wherein the pharmaceutical composition is in the form of a cream.

22. The method defined in claim 18 wherein the pharmaceutical composition is in the form of an ointment.

23. The method defined in claim 18 wherein the pharmaceutical composition is an aerosol.

* * * * *

UNITED STATES PATENT AND TRADEMARK OFFICE
CERTIFICATE OF CORRECTION

PATENT NO. : 4,775,524
DATED : October 4, 1988
INVENTOR(S) : David J. Blythin

It is certified that error appears in the above-identified patent and that said Letters Patent are hereby corrected as shown below:

In column 14, line 38, delete "hvdroxy" and insert --hydroxy--.

In column 14, line 49, delete "O-B-COR'" and insert --O-B-$COR^b$--.

In column 14, line 58, delete " a is an integer" and insert --q is an integer--.

Signed and Sealed this

Twenty-eighth Day of March, 1989

Attest:

DONALD J. QUIGG

Attesting Officer       Commissioner of Patents and Trademarks